United States Patent [19]
Wang et al.

[11] Patent Number: 5,843,459
[45] Date of Patent: Dec. 1, 1998

[54] DIFFERENTIAL INACTIVATION OF NUCLEIC ACIDS BY CHEMICAL MODIFICATION

[75] Inventors: Suming Wang; Charles J. Link, Jr., both of Des Moines, Iowa

[73] Assignee: Human Gene Therapy Research Institute, Des Moines, Iowa

[21] Appl. No.: 587,725

[22] Filed: Jan. 19, 1996

[51] Int. Cl.$^6$ .......................... C12Q 1/70; A61K 39/245
[52] U.S. Cl. .................. 424/231.1; 435/70.3; 435/320.1; 435/173.3; 435/5; 424/93.2
[58] Field of Search ................................ 424/231.1, 93.2; 435/6, 320.1, 5, 70.3, 173.3; 514/455

[56] References Cited

U.S. PATENT DOCUMENTS

| | | | |
|---|---|---|---|
| 5,418,130 | 5/1995 | Platz et al. .................................... | 435/2 |
| 5,459,030 | 10/1995 | Lin et al. ..................................... | 435/2 |

OTHER PUBLICATIONS

Nakashima, et al. 1978. The Journal of Biological Chemistry. vol. 253, No. 24, pp. 8680–8682.
Nakashima, et al. 1979. The Journal of Virology. vol. 32 No. 3 pp. 838–844.
Hermonat, et al. 1984, The Journal of Virology, vol. 51, No. 2 pp. 329–339.
McCoy, et al. 1995. Human Gene Therapy. vol. 6, pp. 1553–1560.
Moroff, G., 1992, Factors Influencing Virus Inactivation and Retention of Platelet Properties Following Treatment with Aminomethyltrimethylpsoralen and Ultraviolet a Light, *Blood Cells* 18:43–56.
Redfield, D., 1981, Psoralen Inactivation of Influenza and Herpes Simplex Viruses and of Virus–Infected Cells, *Infection and Immunity,* Jun. 1981, vol. 32, No. 3, pp. 1216–1226.
Glorioso, J., 1994, Development of Herpes Simplex Virus Vectors for Gene Transfer to the Central Nervous System, *Gene Therapeutic Methods and Applications of Direct Gene Transfer,* Jon A. Wolff, Ed.
Dodd, R.Y., 1991, Inactivation of Viruses in Platelet Suspensions that Retain Their in Vitro Characteristics: Comparison of Psoralen–Ultraviolet a and Merocyanine 540–Visible Light Methods, *Transfusion,* vol. 31, No. 6 pp. 483–490.
Gorin, I., 1989, Brief Communications, *J. Am. Acad. Dermatol,* vol. 20, No. 3, pp. 511–513.
Hanson, C.V., 1978, Photochemical Inactivation of DNA and RNA Viruses by Psoralen Derivatives, *J. of Gen. Virol.,* vol. 40, 345–358, Printed in Great Britain.
Groene, W., 1992, Psoralen Preparation of Antigenically Intact Noninfectious Rotavirus Particles, *J. of Virological Methods,* 38: 93–102.
Dye, K., 1995, Repair of Phage $\lambda$ DNA Damaged by Near Ultraviolet Light Plus 8–Methoxypsoralen, *J. of Gen. Virology,* 76: 723–726.
Cotton, M., 1994, Psoralen Treatment of Adenovirus Particles Eliminates Virus Replication and Transcription While Maintaining the Endosomolytic Activity of the Virus Capsid, *Virology* 205:254–261.
Sastry, S.S., 1993, Psoralens and Their Application to the Study of Some Molecular Biological Processes, *Adv. Enzymology & Related Areas of Molecular Biology,* No. 66, pp. 85–149.
Hönigsmann, H., 1986, Psoralen Photochemotherapy–Mechanisms, Drugs, Toxicity, *Curr. Probl. Derm.,* vol. 15, pp. 52–66.
Hanson, C.V., 1992, Photochemical Inactivation of Viruses with Psoralens: An Overview, *Blood Cells,* 18:7–25.

*Primary Examiner*—James Ketter
*Assistant Examiner*—Irem Yucel
*Attorney, Agent, or Firm*—Zarley, McKee, Thomte, Voorhees, & Sease

[57] ABSTRACT

Disclosed herein is the method for dramatically reducing cytotoxicity of viral vectors such as Herpes simplex viral while retaining gene expression. The method of the invention virtually eliminates the concern of possible recombination during virus propagation and contamination of wild-type virus and virus stock. The invention comprises use of photochemical crosslinking causing differential inactivation of viruses.

21 Claims, 5 Drawing Sheets

DIFFERENTIAL INACTIVATION OF NUCLEIC ACIDS BY CHEMICAL MODIFICATION

FIELD OF THE INVENTION

This invention refers to agents that create nucleic acid base modifications in vitro to allow for the altered control of gene expression and DNA replication within a vector DNA vehicle. This modified DNA can then be used in vitro or in vivo for diagnostic or therapeutic purposes.

BACKGROUND OF THE INVENTION

Virus inactivating agents act in numerous ways. They can act by modifying virus coats, by damaging the virus nucleic acid, or simultaneously through both mechanisms. Formaldehyde and thermal inactivation have been theorized to result from effects involving proteinaceous components than from nucleic acid reactions which occur. Other treatments which include reactions with proteins in addition to traditionally known interactions with nucleic acids include treatment with betapropiolactone, ionizing and non-ionizing radiation and photodynamic inactivation with visible light sensitive dyes.

Inactivation by psoralen derivatives in combination with long wave ultraviolet light has been shown to be effective in both DNA and RNA. The psoralen photochemical reaction involves virus nucleic acid and/or protein. The basic photochemical inactivation process involves joining of two molecular components by a covalent bond achieved through the crosslinking reagents (such as Psoralens), often in the presence of longwave, ultraviolet light. The components may be proteins, peptides, nucleic acids, lipids, carbohydrates, drugs, or any solid particles. Psoralens are a class of furocoumarins including 4,5',8-trimethylpsoralen (TMP), 4'-hydroxymethyl-4,5'-9-trimethylpsoralen (HMT), 4'-aminomethyl-4,5',8-trimethylpsoralen (AMT), isopsoralen and 8-methoxypsoralen (8-MOP). Psoralens readily pass through cell walls as well as virus coats and then can be photoreacted in the various forms of crosslinking, such as DNA to DNA; DNA to RNA; DNA to protein; protein to protein. This photoreaction blocks the process of DNA replication and expression of the virus and therefore, forms the basis of a technique for elimination of the infectivity of viruses. Hanson, C. V., "Photochemical Inactivation of Viruses With Psoralens: An Overview", *Blood Cells*, 1992, 18(1):7–25; Dodd, R. Y., "Viral Inactivation in Platelet Concentrates", *Transfus-Clin-Biol.*, 1994 1(3), p. 181–6; Ronto, G, "Phage Nucleoprotein-Psoralen Interaction: Quantitative Characterization of Dark and Photoreactions", *J. Photochem Photobiol B*, Jan. 1992, 12(1):9–27. It has been used for the prevention of the contamination of virus in blood products through the universal inactivation of viruses, such as human immunodeficiency virus (HIV), Gorin, I., "Successful Treatment of the Pruritus of Human Immunodeficiency Virus Infection and Acquired Immunodeficiency Syndrome With Psoralens Plus Ultraviolet A Therapy", *J Am Acad Dermatol*, Mar 1989, 20(3):511–3; Benade, L. E., "Inactivation of Free and Cell-Associated Human Immunodeficiency Virus in Platelet Suspensions by Aminomethyltrimethylpsoralen and Ultraviolet Light", *Transfusion*, Aug. 1994, 34(8), p. 680–4; Lin, L., "Photochemical Inactivation of Cell-Associated Human Immunodeficiency Virus in Platelet Concentrates", *Blood*, 82, 292–297. 1993, hepatitis virus, Alter, H. J., "Photochemical Decontamination of Blood Components Containing Hepatitis B and Non-A, Non-B Virus", *Lancet*, Dec. 24–31 1988, 2(8626–8627): 1446–50, without destroying valuable blood components Wagner, S. J., "Assessment of the Hemostatic Effectiveness of Human Platelets Treated With Aminomethyltrimethyl Psoralen and UV A Light Using a Rabbit Ear Bleeding Time Technique", *Blood*, Vol. 82, 3489–3492, 1993; Kodd, R. Y., "Inactivation of Viruses in Platelet Suspensions That Retain Their In Vitro Characteristics: Comparison of Psoralen-Ultraviolet A and Merocyanine 540-Visible Light Methods", *Transfusion*, 31(6), 483–490, 1991. Other studies have shown the inactivation in vitro of Herpes simplex virus type 1 (HSV-1) after treatment with psoralen and 1 minute of 320–380 nm UV Redfield, D. C., "Psoralen Inactivation of Influenza and Herpes Simplex Viruses and of Virus-Infected Cells", *Infect Immun*, June 1981, 32(3):1216–26; Hanson, C. V., "Photochemical Inactivation of DNA and RNA Viruses by Psoralen Derivatives", *J. Gen. Virol*, 40, 345–358, 1978, adenovirus Cotten, M., "Psoralen Treatment of Adenovirus Particles Eliminates Virus Replication and Transcription While Maintaining the Endosomolytic Activity of the Virus Capsid", *Virology* Nov. 15, 1994, 205(1):254–61; Cotten, M., "High-Efficiency Receptor-Mediated Delivery of Small and Large (48 Kb) Gene Constructs Using the Endosome Disruption Activity of Defective or Chemically Inactivated Adenovirus Particles", *Proc. Natl. Acad. Sci. USA* 89, 6094–6098, Rouse sarcoma virus (RSV)Swanstrom R., "Interaction of Psoralen Derivatives With the RNA Genome of Rous Sarcoma Virus", *Virology*, 1981, 113(2):613–622, 1981, vesicular stomatitis virus (VSV) Levis, J. T., "Interactions of Psoralen-Derivatized Oligodeoxyribonucleoside Methylphosphonates With Vesicular Stomatitis Virus Messenger RNA", *Antisense Res. Dev.*, Winter 1994, 4(4):223–30. The whole concept of previous studies, however, were to completely kill the viruses by blocking DNA replication and expression of viruses by applying crosslinking agents. According to the invention, blocking of DNA replication and expression can be uncoupled that by using proper amounts of psoralen and UVA. As such viral vectors, such as those based on HSV-1, can be completely inhibited from replicating, but can still maintain gene function as determined by (reporter) gene expression. Also, this crosslinking of virus components, such as DNA, RNA, and proteins was shown to reduce significantly the vector cytotoxicity to host cells. Differential inactivation of viruses with photochemical crosslinking will provide a very useful method for gene therapy, vaccine investigation, immunoassays, organ transplantation and ultimately towards helper virus free system.

It is an object of the present invention to provide a method of inhibiting a plurality viral vectors from replicating while maintaining gene expression by differential gene inactivation.

It is another object of the present invention to provide differential inactivation with photochemical crosslinking.

It is yet another object of the present invention to significantly reduce vector cytotoxicity to host cells.

Other objects will become evident from the description of the invention which follows.

SUMMARY OF THE INVENTION

The invention as disclosed herein is a novel method which dramatically reduces the cytotoxicity of viral vectors such as Herpes simplex virus while retaining gene expression. It virtually eliminates the concern of possible recombination during virus propagation and contamination of wild-type viruses in virus stock because no virus can replicate in any way after treatment. According to the invention the DNA of a virus is damaged by an agent, for example crosslinking may be introduced to the viral vector causing differential inactivation of viruses, by photochemical or other means such as alkylating agents such as 4-hydroperoxycyclophosphamide, cyclophosphamide, Ifosfamide, Melphalan, Busulfan, CCNV (cyclohexyl nitrosovrea), MECCNV (methylcyclohexyl nitrosovrea), BCNV (bis-chlorethyl nitro sovrea), Streptozotocin, Chlorambucil, cis-diamminedichloroplatinum, Carboplatin, aziridinylbenzoquinone, nitrogen mustards, Hepsulfam, Mafosfamide, Ormaplatin, Mitomycin C, hexamethylmelamine and pentamethylmelamine, Thiotepa; DTIC (dacarbazine); MAMSA (amsacrine); Procarbazine; Mitoxantrone; Bleomycin, peplomycin, liblo mycin; pyrazine diazohydroxide; anthrapyrazoles such as piroxantrone, biantrazole; Anthracyclines such as doxorubicin, daunorubicin, epirubicin, idarubicin, S-iminodaunorubicin; dactinomycin, etoposide (VP-16); teniposide (VM-26); dimethyl sulfoxide (DMS); methyl methansulfate (MMS); and (MNNG).

In one embodiment a combination of a furocoumarin crosslinking agent such as a psoralen and ultraviolet radiation are used to provide crosslinking and differential inactivation. Thus the method can be used to deliver foreign genes to cells without fear of activation of virus through recombination. The vector will simply express the foreign genes delivering the products directly to the cell. The method can be used for creation or investigation of highly specific vaccines, immunoassays, organ transplantation and for a helper-free virus system.

DETAILED DESCRIPTION OF THE FIGURES

The files of this patent contains at least one drawing executed in color.

DETAILED DESCRIPTION OF THE INVENTION

Herpes simplex virus type-1 (HSV-1) has been demonstrated as a potential useful gene delivery vector system for gene therapy, Glorioso, J. C., "Development of Herpes Simplex Virus Vectors for Gene Transfer to the Central Nervous System. Gene Therapeutics: Methods and Applications of Direct Gene Transfer", Jon A. Wolff, Editor, 1994 Birkhauser Boston, 281–302; Kennedy, P. G., "The Use of Herpes Simplex Virus Vectors for Gene Therapy in Neurological Diseases", *O J Med*, Nov. 1993, 86(11):697–702; Latchman, D. S., "Herpes Simplex Virus Vectors for Gene Therapy", *Mol Biotechnol*, Oct. 1994, 2(2):179–95. The linear double-stranded DNA genome of HSV-1 is 152 kb in length and encodes more than 72 unique proteins. It has a number of advantages as a vector compared with currently used other gene delivery systems, such as retrovirus and adenovirus. These include its capacity to carry large gene up to about 30 kb, its ability to infect a wide range type of cells and high efficiency of infection and its neural tropism for establish long-term expression in neuron cells.

HSV-1 vectors have been used for transfer of genes to muscle Huard, J., "Herpes Simplex Virus Type 1 Vector Mediated Gene Transfer to Muscle", *Gene Therapy*, 1995, 2, 385–392; and brain, Kaplitt, M. G., "Preproenkephalin Promoter Yields Region-Specific and Long-Term Expression in Adult Brain After Direct In Vivo Gene Transfer Via a Defective Herpes Simplex Viral Vector", *Proc Natl Acad Sci USA*, Sep 13, 1994, 91(19):8979–83, and have been used for murine brain tumor treatment, Boviatsis, E. J., "Long-Term Survival of Rats Harboring Brain Neoplasms Treated With Ganciclovir and a Herpes Simplex Virus Vector That Retains an Intact Thymidine Kinase Gene", *Cancer Res*, Nov 15, 1994, 54(22):5745–51; Mineta, T., "Treatment of Malignant Gliomas Using Ganciclovir-Hypersensitive, Ribonucleotide Reductase-Deficient Herpes Simplex Viral Mutant", *Cancer Res*, Aug 1, 1994, 54(15):3963–6. By contrast retroviral vectors are incapable or poorly infect non-dividing cells such as muscle and neuronal cells. Both retroviral and adenoviral vectors are unable to carry inserts larger than 10 kb and therefore cannot be used in number of gene therapies that require larger capacity, such as Duchenne muscular dystrophy (DMD) where the whole cDNA of which is about 14 kb.

Helper virus dependent mini-viral vectors were developed for easier operation and their capacity for larger insertion (up to 140 kb), Geller, Al, "An Efficient Deletion Mutant Packaging System for Defective Herpes Simplex Virus Vectors: Potential Applications to Human Gene Therapy and Neuronal Physiology", *Proc Natl Acad Sci USA*, Nov 1990, 87(22):8950–4; Frenkel, N., "The Herpes Simplex Virus Amplicon: A Versatile Defective Virus Vector", *Tene Therapy*. 1. Supplement 1, 1994. S40–46; Wang, S., "An Episomal Mini-Viral Vector System for Gene Delivery" (in preparation). The mini-viral vector combines the advantages of a plasmid's easy handling and virus's high efficiency of transferring by infection. The capacity for large inserts makes the vector able to carry large, full length DNA fragments. Larger fragments might allow for functional gene expression to be controlled by its own endogenous elements. Importantly, the mini-viral vector can be designed for the desired mode of action by assembling several elements from different viruses, therefore, creating a hybrid mini-viral vector system. Finally, a helper virus free system could be developed as exists for retroviral and adeno-associated viral vector systems.

Unfortunately, the defective HSV based vectors, or the HSV helper virus show substantial cytotoxicity to infected cells in vitro, Johnson, P., "Cytotoxicity of a Replication-Defective Mutant of Herpes Simplex Virus Type 1", *J. of Virol*, 1992, 66:p.2952–2965. This may be due in part to the toxicity of residual viral proteins produced by the virus. In addition, the virus has the ability to replicate and undergo a lytic cycle in the brain, possibly by recombination or the contamination with wild type, HSV viral sequences of viruses. This potentially could cause Herpes encephalitis leading to fears about its potential safety for ultimate use in humans.

HSV encodes three types of proteins when it infects mammalian cells, i.e. immediate early (IE), early (E) and late (L) gene products. The genes are tightly controlled to ensure the proper expression during the viral life cycle in the form of cascade. Currently used HSV vectors and helper viruses are replication defective viruses. Typically, an essential early gene 3(IE3), that encodes the ICP 4 protein for early and late viral gene expression and virus replication, is deleted from the viral genome, DeLuca, N. A., "Isolation and Characterization of Deletion Mutants of Herpes Simplex Virus Type 1 in the Gene Encoding Immediate-Early Regulatory Protein ICP4", *J. of Virol*, 1985. 56:p.558–570; DeLuca, N. A., "Activities of Herpes Simplex Virus Type 1 (HSV-1) ICP4 Genes Specifying Nonsense Peptides", *Nucleic Acids Res.*, 1987. 15:p.4491–4511. The defective virus (helper virus) cannot replicate in normal cell cultures and human body because of the lack of IE 3 genes in the virus. The defective virus has to be first transfected into helper cell line which contains IE3 gene for complementation. In the case of mini-viral vector, the vector is first transfected into a helper cell line. This transfected helper cell line is then infected by replication-incompetent helper virus (deletion mutant) and this induces virion propagation in the infected cells.

Ultraviolet (UV) light has been used to irradiate the virus and shown to reduce cytotocixity Johnson, P., "Cytotoxicity of a Replication-Defective Mutant of Herpes Simplex Virus Type 1", *J. of Virol*, 1992, 66:p.2952–2965; Leiden, J. M., "Identification of the Herpes Simplex Virus DNA Sequences Present in Six Herpes Simplex Virus Thymidine Kinase-Transformed Mouse Cell Lines", *J. Virol*, 33.272–285, 1980; Wang, S., "An Episomal Mini-Viral Vector System for Gene Delivery" (in preparation). However, the UV light alone only interacts with the viral DNA and does not eliminate the viral cytotoxicity caused by structural components of the virion. The large amount of UV exposure required totally inhibits both viral replication and gene expression, while small amount of UV exposure induce DNA damage that can be efficiently removed or repaired by the host cell, DNA excision repair system. The viral cytotoxicity still remains.

Disclosed herein in a novel method that dramatically reduces the cytotoxicity of the virus while the gene expression of the virus still remains. In addition, this method prohibits replication of the virus in the helper cell line which contains IE3 gene for complementation. It eliminates the concern of the possible recombination during the virus propagation and potential contamination of wild type of viruses in virus stock.

It also greatly reduces any possible recombination between the helper virus and the latent infectious virus in the human body when used for future gene therapy, since the numbers of IE 3 genes, if existent in the human body, are far below the level in E5 cells (each cell has an IE3 gene). Ultimately, this invention will allow for the safe use of HSV and HSV mini-viral vectors in human gene therapy applications. It also provides a novel way of producing nucleic acid based vaccines since the inactivated vectors still expresses certain genes, but are unable to replicate. An example of an application would be to use psoralen modified HSV virus to prevent its replication, but allow for some HSV gene expression. It has been demonstrated that one of HSV IE gene products, ICP 47, could disturb the antigens presentation of cellular major histocompatibility complex (MHC) system, York, I. A., "A Cytosolic Herpes Simplex Virus Protein Inhibits Antigen Presentation to CD8+ T Lymphocytes", *Cell* 77, 525–535. 1994. The replication inactivated, gene expression permissive HSV can be used for protection of a transplanted organ against in situ immunoreactivity.

Thus the method involves treating a viral vector with an effective amount of a crosslinking agent so that replication of the virus is inhibited. This can be used with any type of viral vector system such as adenoviral, adeno-associated viral, HSV, papilloma, retroviral, EBV are some representative viral systems which can be used according to the method of this invention. As used herein the term "an effective amount" shall mean an amount sufficient to inhibit replication of the viral vector while maintaining gene expression. This amount can be determined for any system by the methods disclosed herein but briefly involve use of a reporter gene in said vector, the expression of which can be observed. For example disclosed herein is use of the lac-Z reporter gene and observation of gene product by assaying for $\beta$-galactosidase activity by staining. Other such reporter gene expression detection systems include alkaline phosphatase, chloramphenical acetyl transferase, green flourescent protein, or other proteins expressed and then detected by conjugated antibody systems. The in vitro protocol then involves varying the amount of crosslinking agent and observing gene expression to identify the effective range. This is done in combination with traditional cell staining to identify cell lysis. Contrary to prior thought a balance between inactivation of gene expression and complete virus replication so that the two can be uncoupled by treatment by the method of the invention so that one can be achieved without the other.

In a preferred embodiment the crosslinking agent is a psoralen derivative either natural or synthetic such as psoralen, 8-methoxypsoralen, 4,5',8-trimethylpsoralen, 4'-hydroxymethyl-4-5'-8 trimethylpsoralen, 4'-aminomethyl-4,5'8-trimethylsporalen, isopsoralen, and 8 methorypsoralen. The psoralen can be delivered to the cells in a solution with a buffer such as phosphate. Psoralen compounds are polycyclic planar molecules with an affinity for nucleic acids. They readily pass through virus coats, and can thus react with nucleic acids inside.

In a more preferred embodiment the invention also comprises treatment with an effective amount of long wavelength ultraviolet radiation (LWUV) in combination with the crosslinking agent to further enhance the crosslinking effect. Thus the present invention contemplates, in some embodiments, use of a photodiaclivation device capable of emitting a given intensity of a spectrum of electromagnetic radiation comprising wavelengths between 180 nm and 400 nm, and in particular, between 300 nm and 400 nm. When a psoralen-nucleic acid complex is irradiated with LWV in approximately 300–400 nm a photochemical reaction occurs which results in the covalent addition of the psoralen to a pyrimidine or purine base. Psoralens intercalate between the bases of nucleic acids and form covalent, cyclobutane-type linkages. Psoralen photoreaction is not accelerated at higher temperatures and may, in fact be enhanced at lower temperatures which stabilize nucleic acid secondary structures. All reactions herein are performed at standard temperature and pressure unless otherwise indicated. For a review of psoralen and photodiactivation of viruses including their reaction kinetics, see Hansen, Carl "Photochemical Inactivation of Viruses With Psoralus: An Overview", *Blood Cells* (1992) 18:7–25, incorporated herein by reference. The appropriate combination of crosslinking agent and LWUV radiation can again be determined in vitro for any particular viral vector as shown herein and explained earlier using grids as shown in Table 1 of the Example section.

Without wishing to be bound by any theory it is postulated that the crosslinking agent acts in randomly inactivating different portions of the vector. When a plurality of vectors are so treated the inactivated regions are complemented by the presence of other vectors with a different region inactivated retaining overall expression yet prohibiting replication of any single vector.

In a most preferred embodiment the vector is a Herpes simplex virus type-1 vector which is treated with from about 0.1 to about 1 mg/ml TMP with from about 2 to 8 minutes of UVA irradiation. The best combination with the CgalΔ3 and pHE-lac helper virus was 1 mg/ml TMP with 4 minutes of UVA radiation.

The following examples are for illustration purposes only and are not intended to limit the invention. Those of skill in the art will appreciate that various permutations can be achieved without altering the intended result and in fact are intended to be within the scope of this invention.

EXAMPLES

MATERIALS AND METHODS

Figure 9A:
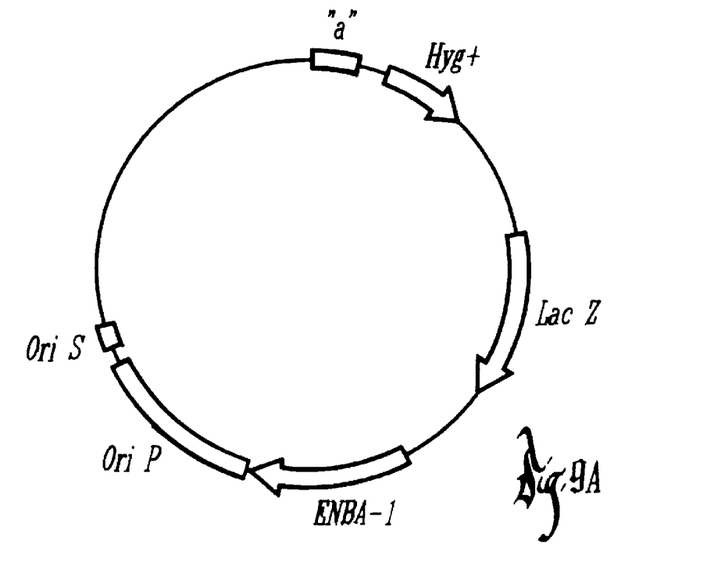
FIGS. 9A and 9B are representations of the vectors of the invention.
Figure 9B:
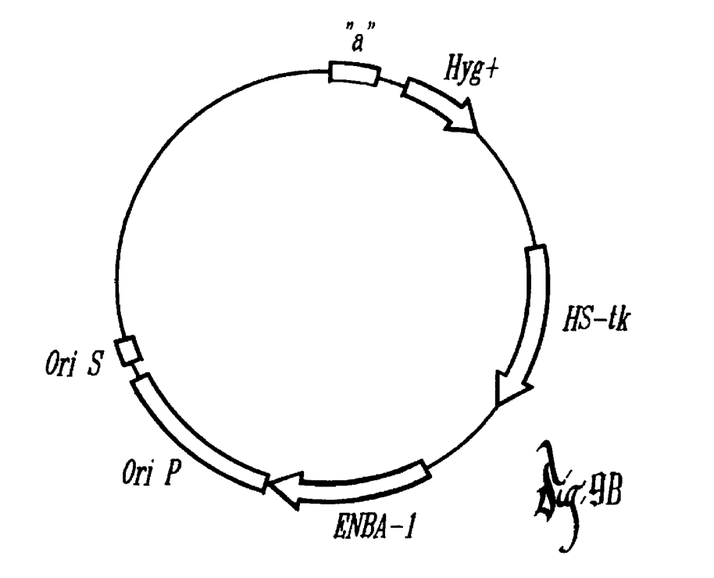

The mini-viral vector and viruses:

An HSV mini-viral vector pHE-lac was obtained by inserting bacterial lac-Z gene into multi-cloning sites of pHE mini-viral vector. The pHE vector is a helper dependent HSV derived mini-viral vector which combines HSV genes with EBV genes for maintenance of the virus in episomal form and very high transfection efficiency. The vector construction is shown in FIG. 9A. The lac-Z gene expressing β-galactosidase was under the control of the human cytomegalovirus (CMV) immediate early promoter. The helper virus, HSV-1 strain 17+ IE3 deletion mutant D120 (kindly provided by Dr. Neal Deluca, University of Pittsburgh) was used for propagation of pHE-lac (contains β-galactosidase) and pHE-tk (Herpes Simplex thymidine kinase) mini-viral vectors. The HSV vector CgalΔ3 that carried a reporter gene, lac-Z, derived from HSV-1 strain 17+ IE3 deletion mutant D30EBA was kindly provided by Dr. P. Johnson, Univ. of California San Diego, Calif. The lac-Z gene expression in these vectors have been demonstrated for the β-galactosidase activity in infected cells including a number of tumor cells. The efficiency of infection can be as high as 95 to 100% in cultured human fibroblast cells and epithelial cells (Wang and Link, unpublished observations). pHE-tk was obtained by inserting herpes simplex virus thymidine kinase gene (HSV-tk) into the multi-cloning site of the pHE mini-viral vector. The tk gene is driven by human cytomegalovirus (CMV) immediate early promoter FIG. 9B.

Cell lines and cell culture conditions:

All cells were grown and maintained in DMEM (GibcoBRL) containing 10% fetal bovine serum (FBS, Gibco), glutamine and penicillin/streptomycin, and incubated at 37° C. in a humidified, 5% $CO_2$ incubator. The helper cell line. E5 is derived from African green monkey cells (Vero) and incorporated with IE3 gene of HSV in cell genome (kindly provided by Dr. Neal A. DeLuca, University of Pittsburgh). The cells were maintained with 400 mg/ml G-418 (Geneticin®, GibcoBRL). T98G is fibroblast-like cells derived from human glioblastoma. IGROV is a human ovarian carcinoma cell line.

Packaging and preparation of Herpes vector stocks:

The hygromycin resistant colonies which contained pHE-lac and pHE-tk in episomal form were trypsinized and $3 \times 10^6$ cells were plated on a 10-cm dish. After cells grew to confluence, 0.1 multiplicity of infection (MOI) of helper virus (d120) in 1 ml of Opti-MEM (Gibco, BRL) was added to the dish. The vectors were allowed to adsorb to the cells for 3 hours at 37° C. in a humidified, 5% $CO_2$ incubator. The virus solutions were aspirated and 10 ml of DMEM with 10% of FBS was added and incubated for three days at 37° C. in a humidified, 5% $CO_2$ incubator. The supernate containing viral vector and cell debris was collected and centrifuged. The vector containing supernate was used for virus titration and infection. For production of helper virus, 0.025 MOI helper virus was used.

Psoralen treatment and UVA irradiation of virus (PUVA):

4,5',8-trimethylpsoralen (TMP, Trioxsalen) was purchased from Sigma. Various concentrations of TMP (0.01–2 μg/ml) were added to stock of packaged pHE-lac, pHE-tk and CgalΔ3 30 minutes before UVA irradiation and kept in 37° C. The treated virus stocks then were irradiated with UVA sources (365 nm) at various dosages. The effect of psoralen and UVA irradiation (PUVA) treatment on virus DNA replication and gene expression of pHE-lac, pHE-tk and CgalΔ3 were determined by infection of cells originally titered at 3 MOI. The β-galactosidase activity was determined by 5-bromo-4-chloro-3-indolyl-B-D-galactopyranoside (X-gal) (Promega) staining and O-Nitrophenyl-b-D-galactopyranoside (ONPG) quantity measurement were carried out the following day after infection. The tk gene activity of pHE-tk was determined by cell proliferation assay.

In vitro infection with pHE-lac, pHE-tk and CgalΔ3:

For in vitro infection, E5 and cultured human cells T98G and IGROV were trypsinized, counted and seeded (at appropriate densities). When the cells were confluent, the TMP treated viral stocks were incubated with the cells at MOI for 3 hours. The β-galactosidase and tk activity was measured 24 hours later for in vitro infection.

Assay for β-galactosidase activity:

Two assays were used to detect β-galactosidase activity in pHE-lac and CgalΔ3 infected cells. For visualization of virions carrying lac-Z gene, infected cells were rinsed with PBS on the second day following infection. The cells were then fixed for 5 minutes at room temperature in 2% Formaldehyde, 0.3% glutaraldehyde in PBS, and stained by incubating in a chromophore solution containing 0.1% X-Gal (5-bromo-4-chloro-3-indolyl-B-D-galactopyranoside)(Promega), 5 mM $K_4Fe(CN)_6 3H_2O$, 5 mM $K_3Fe(CN)_6$, and 2 mM $MgCl_2$ in PBS. Incubation continued at 37° C. until color developed (usually within 30 to 60 minutes). For quantitative measurement of β-galactosidase activity, after 48 hours of infection, all cells were trypsinized and washed once in PBS solution and $1.0 \times 10^6$ cells were resuspended in an ONPG lysis solution (0.45 mM O-Nitrophenyl-b-D-Galactopyranoside and 0.5% Nonidet P-40 in HBSS). Cell lysates were then incubated at 37° C. in a 5% $CO_2$ humidified incubator, and the optical density (OD) at 420 nm was measured 1 hour later.

Titration and plaque forming assay:

The virus stocks were diluted in 100 ml Opti-MEM media and the $10^{-3}$ to $10^{-8}$ dilutions were used to infect confluent monolayers of E5 cells grown in 6-well plates. The viruses were allowed to adsorb to the cells for 2 hours at 37° C. in a humidified, 5% $CO_2$ incubator. The virus solutions were aspirated and washed with Hank's solution and overlaid with 2 ml DMEM containing 5% FBS and 0.3% methycellulose and then placed at 37° C. in a humidified, 5% $CO_2$ incubator for 3 days. Plaques were visualized by staining with 0.5 ml of 0.6% crystal violet for 10 minutes. The plates were dried and the plaques were counted. The titers were determined as the plaque forming unit per milliliter (pfu/ml) from the number of plaques in a well times dilution factor.

Cell proliferation assay: In vitro inhibition studies of pHE-tk vector on nontransduced tumor cells after ganciclovir treatment In vitro HStk proliferation assays were performed to characterize further the nature of the potentiation of GCV toxicity after transduction with pHE-tk vector, HSV vector, or no vector. Cell mixtures were plated of tumor cells that were harvested from 80–90% confluent cultures by trypsin digest, counted and plated at $10^4$ cells/well in 200 $\mu$l DMEM with 10% fetal calf serum (FCS) media (Gibco, BRL)(in 96 well flat-bottom plates (costar). Three replicate samples were plated for each condition. The cells were incubated overnight at 37° C. in DMEM supplemented with 10% fetal calf serum. GCV (Syntex, Palo Alto, Calif.) was then added at a concentrations of 0 or 5.1 $\mu$g/ml. Forty-four hours later 0.5 $\mu$Ci [$^3$H]-thymidine (New England Nuclear) was added to each well and the cells were incubated at 37° C. for an additional 4 hours. Cells were then trypsin digested for 15–20 minutes at 37° C., then the plates were washed and transferred to filter mats in a Tomtec cell harvester. Filter mats were then counted. The amount of incorporated $^3$[H]-thymidine is measured as counts per minute (cpm). Each condition was cultured in triplicate wells and the values expressed as a percent of control (no GCV).

RESULTS

PUVA treatment totally inhibits virus replication while lac-Z gene expression remained:

E5 cells were plated into 24 well plates at a density of $1.5 \times 10^5$/well. The cells were infected with PUVA treated Cgal$\Delta$3 and pHE-lac/helper virus the following day (Table 1).

TABLE 1

The PUVA Dosages Used To Treat Cgal$\Delta$3 For Infection
(1 minute = 500 J/m$^2$ @ 365 nm)

|   |            | 1   | 2   | 3   | 4   | 5   | 6        |
|---|------------|-----|-----|-----|-----|-----|----------|
| A | TMP (mg/ml)| 0   | 0   | 0   | 0.1 | 1.0 | No       |
|   | UVA (mins) | 0   | 1   | 10  | 0   | 0   | virus    |
| B | TMP (mg/ml)| 0.1 | 0.5 | 1.0 | 0.1 | 0.5 | 1.0      |
|   | UVA (mins) | 1   | 1   | 1   | 2   | 2   | 2        |
| C | TMP (mg/ml)| 0.1 | 0.5 | 1.0 | 0.1 | 0.5 | 1.0      |
|   | UVA (mins) | 4   | 4   | 4   | 6   | 6   | 6        |
| D | TMP (mg/ml)| 0.1 | 0.5 | 1.0 | 0.1 | 0.5 | 1.0      |
|   | UVA (mins) | 8   | 8   | 8   | 10  | 10  | 10       |

Figure 1:
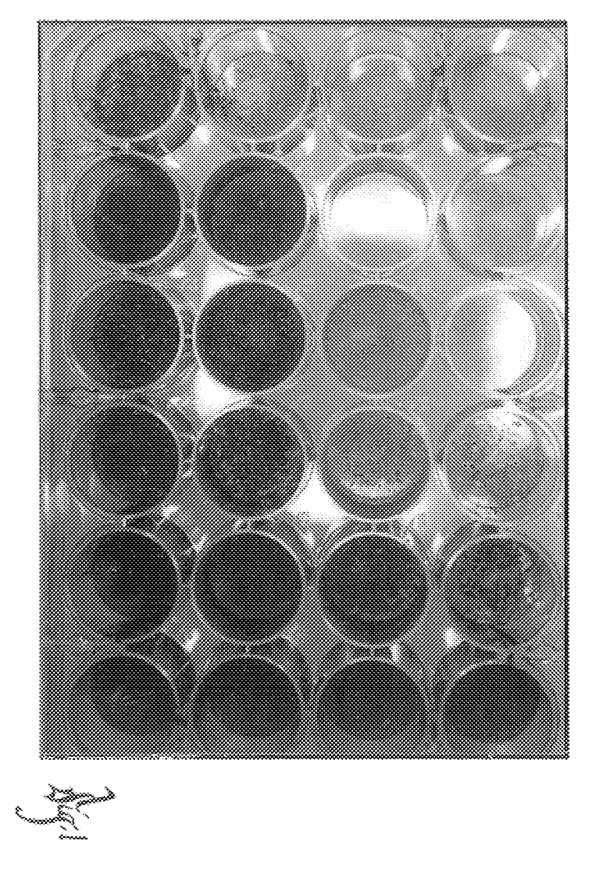
FIG. 1 is a photograph of stained E5 helper cells infected with CgalΔ3 which was treated at varying concentrations of 4,5',8-trimethylpsoralen and time of exposure to ultraviolet light according to Table 1.
Figure 2:
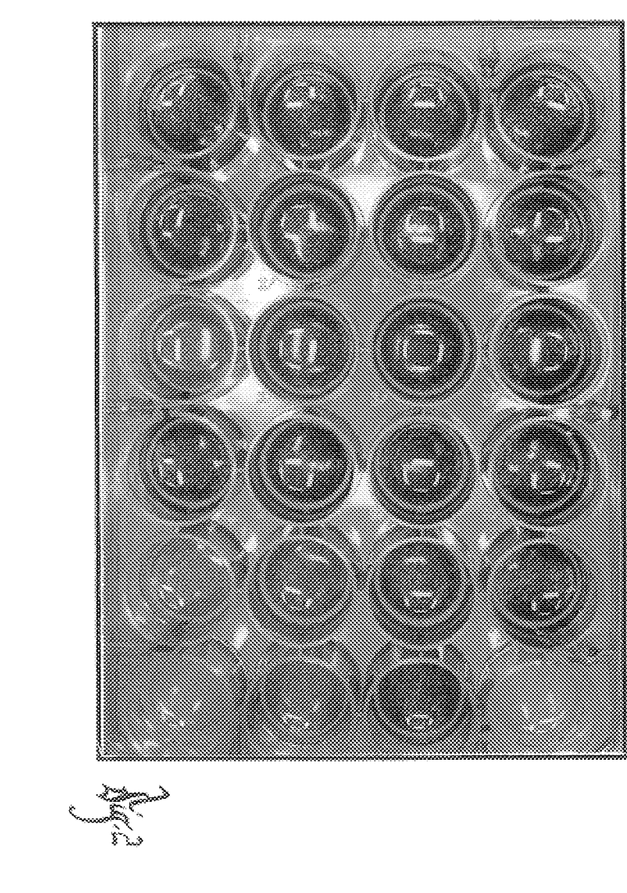
FIG. 2 is a photograph of X-gal stained T98G cells infected with CgalΔ3 which were treated with varying dosages of 4,5,'8 trimethylpsoralen and time of exposure to ultraviolet light according to Table 1.
Figure 3:
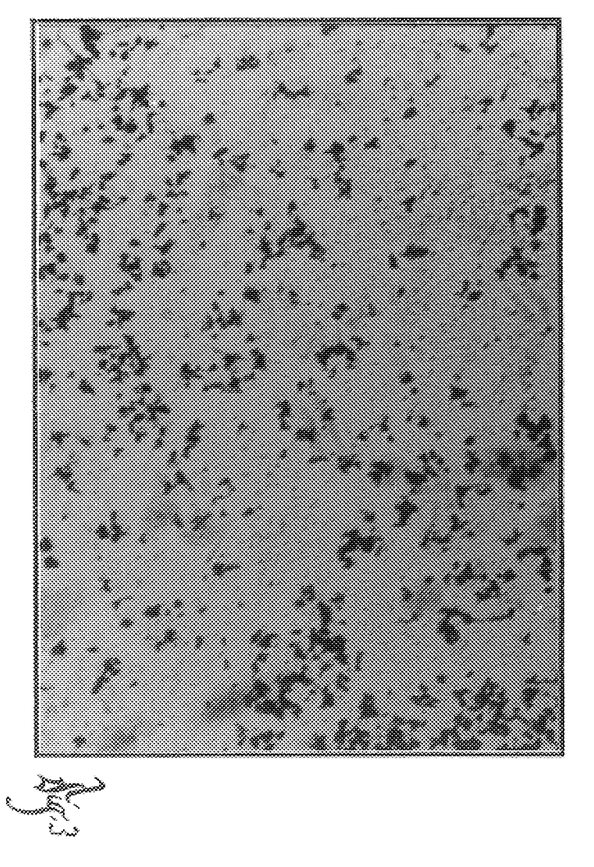
FIG. 3 is a photograph of the E5 cells infected with CgalΔ3 treated with no 4,5',8-trimethylpsoralen (TMP) and no ultraviolet exposure.
Figure 4:
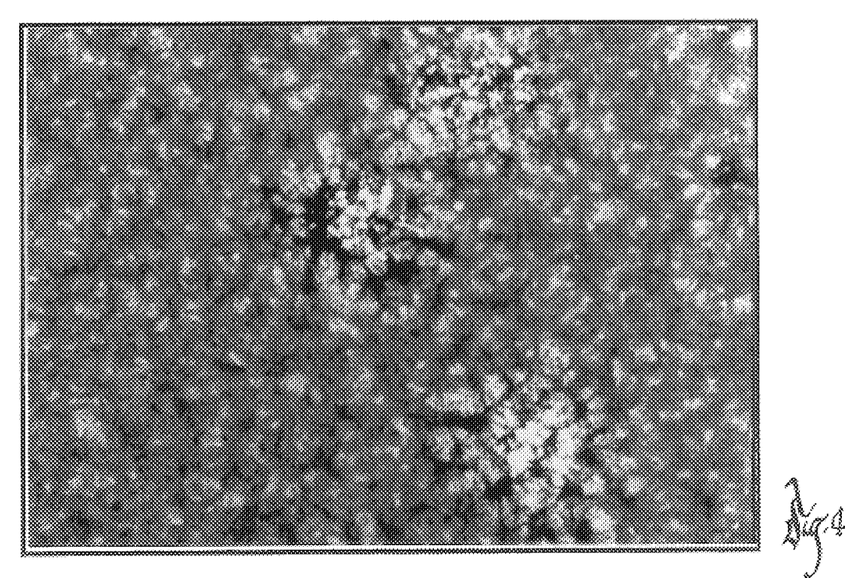
FIG. 4 is a photograph of E5 cells showing plaque formation after infection with CgalΔ3 which was treated with 0.5 mg/ml of TMP and 4 minutes UVA irradiation.
Figure 5:
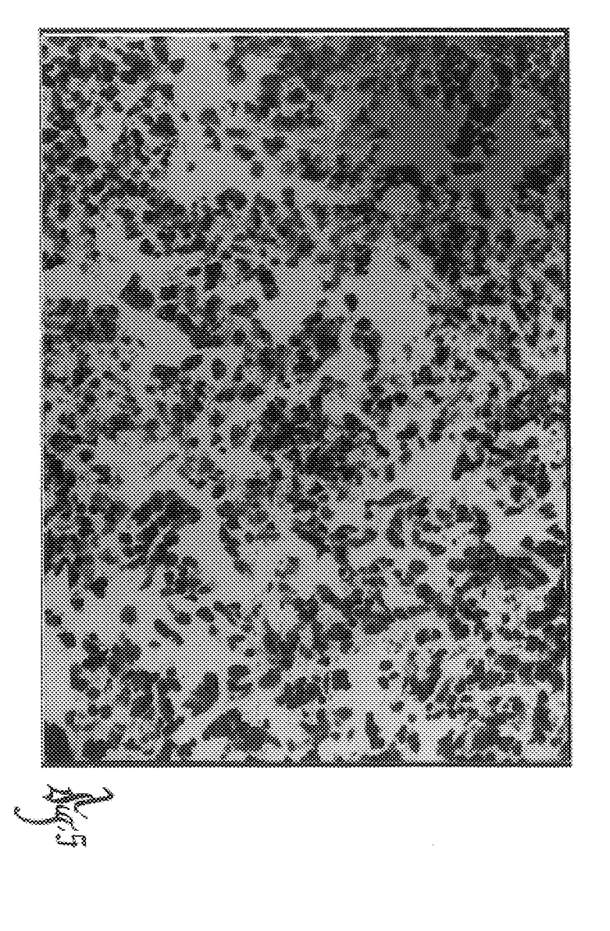
FIG. 5 is a photograph of X-gal stained of T98G cells infected with CgalΔ3 which was treated with 1.0 mg/ml TMP plus 4 minutes UVA.
Figure 6:
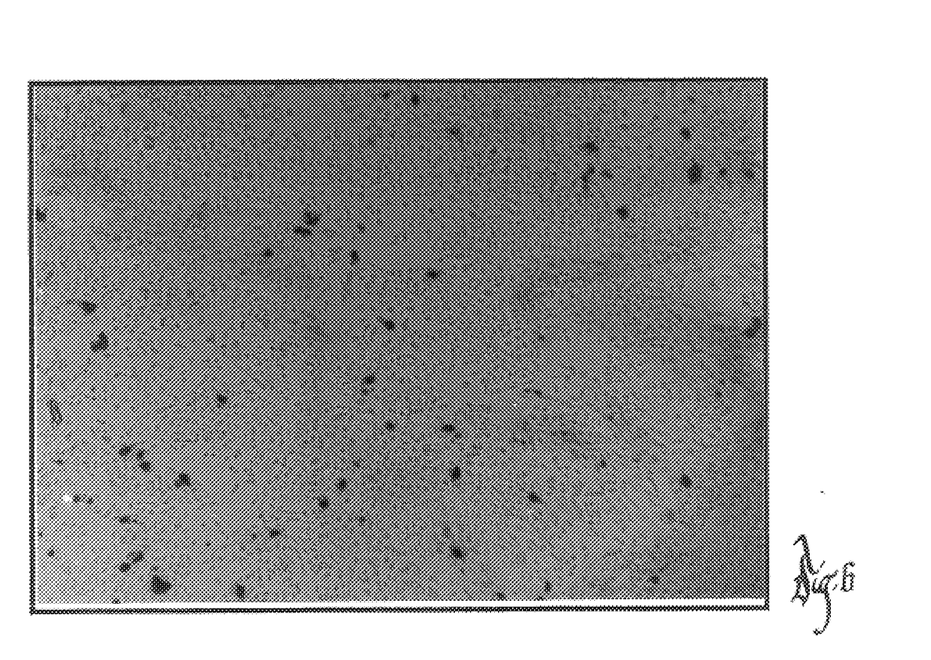
FIG. 6 is a photograph of X-gal staining of T98G cells infected with CgalΔ3 and treated with 1.0 mg/ml TMP plus 10 minutes UVA irradiation.
Figure 7:
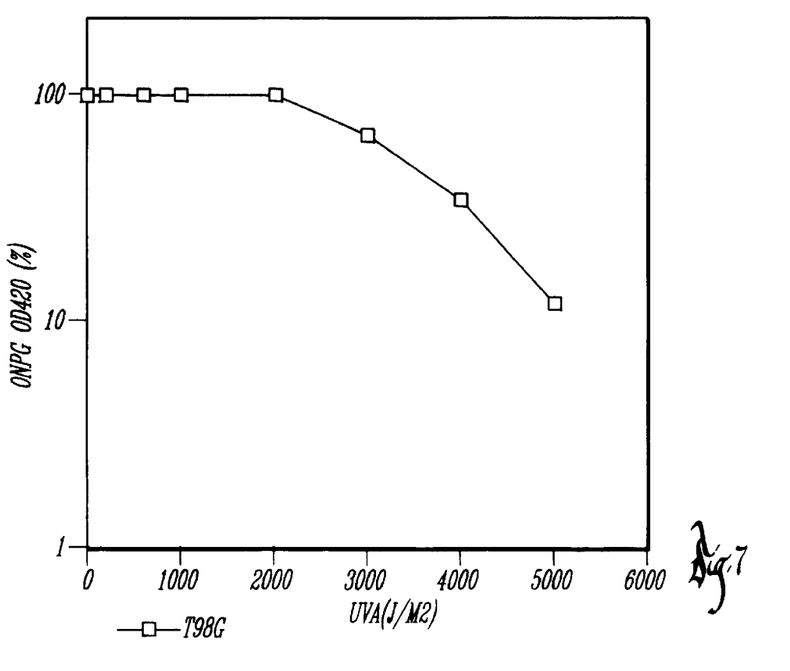
FIG. 7 is a graph depicting the ONPG data representing β-galactosidase activity of CgalΔ3 virus over varying doses of PUVA.

After three days incubation, the cells were stained. The E5 cells are helper cell line which contains HSV IE 3 gene that can complement Cgal$\Delta$3. At PUVA zero dosage (TMP 0 mg/ml and UVA 0 minute irradiation), Cgal$\Delta$3 virus goes into a lytic replication cycle. Most of the E5 cells were lysed so that there were no cells stained (FIG. 1, the PUVA dosages corresponding to Table 1)(row A, column 1). The UVA or TMP alone do not effectively inhibit virus replication (lytic cycle) (FIG. 1) See row A columns 2 and 3 and row A columns 4 and 5. However, the differential combination of TMP and UVA does inhibit viral replication. The inhibition depends on the dosage of PUVA (FIG. 1). The same treated virus stocks were used to infect T98G cells and the cells were stained the following day to show lac-Z gene expression (dosages see Table 1). The cells with $\beta$-galactosidase activity representing lac-Z gene expression are stained blue by X-gal. FIG. 2 shows the result. At low dosages of PUVA treatment, the lac-Z gene expression was as high as zero control (row A, column 1). TMP or UVA treated only have similar level of lac-Z gene expression (row A, columns 2 and 3 and row A columns 4 and 5). However, at this dosages of PUVA, the viral replication cannot be prohibited (FIG. 1). Higher PUVA dosages totally inhibited viral replication but the lac-Z gene expression was also reduced (FIG. 2). The comparison of FIG. 1 and 2 shown that at certain dosages, such as TMP at 1.0 mg/ml and UVA for 4 minutes irradiation (2000 J/m$^2$), the Cgal$\Delta$3 virus replication was totally inhibited but the lac-Z gene expression remained high. FIG. 3 is a 40X magnification showing the lysed E5 cells at PUVA dosage 0/0 (TMP/UVA) after viral replication. FIG. 4 shows that a few viral plaques formed after infection of Cgal$\Delta$3 virus treated by PUVA at dosage 0.5 mg/ml of TMP plus 4 minutes UVA irradiation. FIG. 5 shows X-gal staining of T98G cells infected with Cgal$\Delta$3 virus treated by PUVA at a dosage of 1.0 mg/ml of TMP followed by 4 minutes UVA irradiation (2000 J/m$^2$). Nearly all the cells show blue staining indicating that lac-Z gene of Cgal$\Delta$3 virus maintains high level of expression. FIG. 6 shows X-gal staining of T98G cells infected with Cgal$\Delta$3 virus treated by PUVA at a dosage 1.0 mg/ml of TMP followed by 10 minutes UVA irradiation (5000 J/m$^2$). Few cells show blue staining indicating that the lac-Z gene of Cgal$\Delta$3 virus was inhibited by the greater PUVA treatment. FIG. 7 gives the ONPG data that represents the $\beta$-galactosidase activity of Cgal$\Delta$3 virus after UVA irradiation when all samples were exposed to 1.0 mg/ml of TMP. A similar experiment was carried out by using pHE-lac mini-viral vector system and the similar results were obtained. Indicating that the amounts of the TMP/UVA required to block viral replication but permit gene transcription was not virus dependant.

Figure 8:
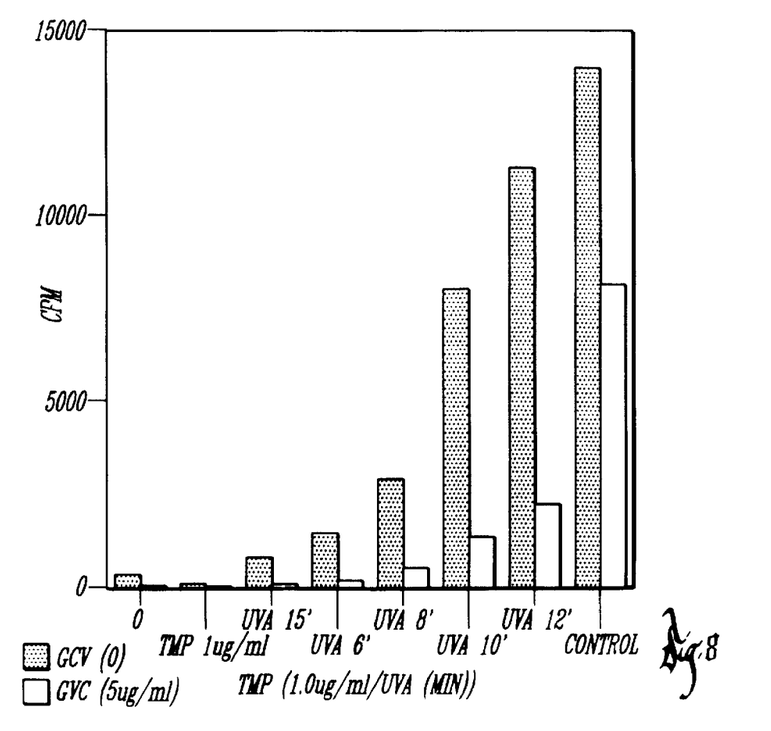
FIG. 8 is a graph depicting cell proliferation after exposure to Herpes viral vector, measured by 3H-thymidine incorporation. Vectors were prepared by TMP exposure (1 mg/ml) and differing lengths of UV exposure (0–12 min.). Each sample is shown with no ganciclovir and with 5 μg/ml ganciclovir illustrating the decrease in cytotoxicity while still expressing functional Herpes thymidine kinase activity.

PUVA treatment reduced cytotoxicity of HSV virus:

The cytotoxicity of Cgal$\Delta$3 virus and helper virus were tested by cell proliferation assays. The proliferation of vital cells is reflected by the cells incorporating a certain amount of [$^3$H] thymidine during cellular DNA synthesis. The reduced cellular DNA synthesis correlates with reduced cell viability secondary to cytotoxicity caused from infection by viruses. IGROV cells, derived from a human ovarian carcinoma, were infected with pHE-tk viral stock containing helper virus d120. The viral stock was treated with PUVA (all samples exposed to TMP at 1.0 mg/ml but various UVA irradiation doses). The PUVA untreated virus significantly reduced the infected cells' DNA synthesis (FIG. 8) indicating that the infected cells did not metabolize normally and the cells were not viable and were eventually going to die. This phenomenon has limited the use of HSV virus as a gene deliver vector in human gene therapy. However, cells infected with the PUVA treated virus significantly recover their DNA synthetic rate and vitality with increased PUVA dosages (FIG. 8). While the cytotoxicity of virus was reduced to near that of normal control cells not exposed to virus, the tk gene that was carried by the mini-viral vector still remained functional. The product of tk gene, Herpes Simplex thymidine kinase, converts ganciclovir (GCV) into a toxic form by phosphorylating GCV. The phosphorylated GCV leads to inhibition of cell growth and eventually induces cell death. The recovered DNA synthesis of pHE-tk infected cells by PUVA treatment was reduced again when GCV was added indicating that PUVA treatment prevented helper virus' mediated cytotoxicity but did not inhibit the normal expression of carrier gene, i.e. tk gene in this case.

As can be seen from the foregoing the invention accomplishes at least all of its objectives.

What is claimed is:

1. A method of reducing cytotoxicity while retaining gene expression of Herpes Simplex Virus (HSV) vectors comprising:

treating a plurality of said HSV vectors with an effective amount of a psoralen compound and an effective amount of ultraviolet (UV) radiation, so that random crosslink lesions are formed causing inhibition of replication while gene expression is retained.

2. The method of claim 1 wherein said vector is a Herpes Simplex Virus-type 1 vector.

3. The method of claim 1 wherein said HSV vector is an HSV mini-viral vector.

4. The method of claim 1 wherein said psoralen compound is selected from the group consisting of 4,5',8-trimethylpsoralen, 4'-hydroxymethyl-4,5'-8-trimethylpsoralen, 4'-aminomethyl-4,5',8-trimethylpsoralen, isopsoralen and 8-methoxypsoralen.

5. The method of claim 1 wherein said psoralen compound is 4,5',8-trimethylpsoralen.

6. The method of claim 5 wherein said psoralen compound is in an amount of from about 0.1 $\mu$g/ml to 2.0 $\mu$g/ml.

7. The method of claim 1 wherein said exposure to UV radiation is from about 500 J/m$^2$ to 10$^4$ J/m$^2$.

8. A method of inhibiting replication of a viral vector stock while retaining gene expression, comprising:

a) determining an effective amount of a nucleic acid damaging agent which induces random crosslink lesions, said agent comprising a crosslinking agent and an effective amount of UV radiation, which inhibits replication while retaining gene expression of a viral vector as characterized by assaying for the presence of a reporter gene product and assaying for cell lysis, and thereafter;

b) treating said viral vector stock with said effective amount of said crosslinking agent, and;

c) further treating said viral vector stock with said effective amount of UV radiation.

9. The method of claim 8 wherein said reporter gene is selected from the group consisting of a lac-Z gene, a HSV-tk gene, or a Green Fluorescent Protein gene.

10. The method of claim 8 wherein said crosslinking agent is a furocoumarin of the class psoralen.

11. The method of claim 8 wherein said crosslinking agent is 4,5',8-trimethylpsoralen.

12. The method of claim 8 wherein said UV exposure is ultraviolet-A (UVA) at a wavelength of between about 320 nm to about 400 nm.

13. The method of claim 12 wherein said UV exposure is at a wavelength of 365 nm.

14. The method of claim 8 wherein said viral vector stock is selected from the group consisting of a retroviral vector, an adeno viral vector, an adeno-associated viral vector, vaccinia viral vector, para influenza viral vector or a Herpes Simplex Virus vector.

15. The method of claim 8 wherein said viral vector stock is a Herpes Simples Virus-type 1 vector.

16. A viral vector stock with decreased cytotoxicity produced by the method of:

treating said viral vector stock with an effective amount of a crosslinking agent, and thereafter exposing said vector to ultraviolet (UV) radiation so that random crosslink lesions are formed.

17. The viral vector stock of claim 12 wherein said crosslinking agent is a psoralen compound.

18. The viral vector stock of claim 12 wherein said viral vector is a Herpes Simplex Virus viral vector.

19. The viral vector stock of claim 17 wherein said psoralen compound is 4,5',8-trimethyl psoralen TMP.

20. A viral vector stock with decreased cytotoxicity and retained gene expression produced by a method of random crosslink lesions which inhibit replication of Herpes Simplex Virus (HSV) vector stock while retaining gene expression, comprising:

a) treating a plurality of HSV vectors with about 0.1 $\mu$g/ml 4,5',8-trimethyl psoralen;

b) further treating said plurality of HSV vectors with ultraviolet-A (UVA) at a wavelength between about 320 nm and 400 nm.

21. A method of inhibiting replication of a viral vector stock while retaining gene expression, comprising:

a) determining an effective amount of a nucleic acid damaging agent which induces random crosslink lesions, thus inhibiting replication while retaining gene expression of a viral vector as characterized by assaying for the presence of a reporter gene product and assaying for cell lysis, and thereafter;

b) treating said viral vector stock with said effective amount of said crosslinking agent, and;

c) further treating said viral vector stock with said effective amount of UV radiation.

* * * * *